US009207235B2

(12) United States Patent
Sugimura et al.

(10) Patent No.: US 9,207,235 B2
(45) Date of Patent: Dec. 8, 2015

(54) NUCLEIC ACID ANALYZER, REACTION DEVICE FOR NUCLEIC ACID ANALYSIS AND SUBSTRATE OF REACTION DEVICE FOR NUCLEIC ACID ANALYSIS

(75) Inventors: Yoshiaki Sugimura, Hitachinaka (JP); Masatoshi Narahara, Hitachinaka (JP); Kazumichi Imai, Hitachinaka (JP); Toshiro Saito, Hitachinaka (JP); Ryoji Inaba, Hitachinaka (JP); Takuya Matsui, Mito (JP)

(73) Assignee: Hitachi High-Technologies Corporation, Tokyo (JP)

( * ) Notice: Subject to any disclaimer, the term of this patent is extended or adjusted under 35 U.S.C. 154(b) by 289 days.

(21) Appl. No.: 13/575,564

(22) PCT Filed: Dec. 1, 2010

(86) PCT No.: PCT/JP2010/007001
§ 371 (c)(1),
(2), (4) Date: Jul. 26, 2012

(87) PCT Pub. No.: WO2011/092780
PCT Pub. Date: Aug. 4, 2011

(65) Prior Publication Data
US 2012/0316087 A1    Dec. 13, 2012

(30) Foreign Application Priority Data

Jan. 28, 2010    (JP) ................. 2010-016140

(51) Int. Cl.
*B01L 3/00* (2006.01)
*G01N 33/543* (2006.01)
(Continued)

(52) U.S. Cl.
CPC .... *G01N 33/54313* (2013.01); *B01L 3/502715* (2013.01); *G01N 21/648* (2013.01);
(Continued)

(58) Field of Classification Search
CPC ................. B01L 2200/0668; B01L 2300/0819
USPC ................... 422/552, 553, 551, 503; 436/527
See application file for complete search history.

(56) References Cited

U.S. PATENT DOCUMENTS 5,587,128 A * 12/1996 Wilding et al. ................. 422/50
5,707,799 A * 1/1998 Hansmann et al. .......... 435/6.11
(Continued)

FOREIGN PATENT DOCUMENTS

JP    2008-190937 A    8/2008
JP       2009-70 A    1/2009
(Continued)

OTHER PUBLICATIONS

J. Ju et al., Four-Color DNA Sequencing by Synthesis using Cleavable Fluorescent Nucleotide Reversible Terminators, PNAS, vol. 103, Dec. 26, 2006, pp. 19635-19640 (six (6) sheets).
(Continued)

*Primary Examiner* — Natalia Levkovich
(74) *Attorney, Agent, or Firm* — Crowell & Moring LLP

(57) ABSTRACT

Provided is a reaction device for nucleic acid analysis wherein microparticles, which carry a nucleic acid to be detected having been immobilized thereon, are aligned in a lattice form on a substrate according to the pixel size of a two-dimensional sensor. By this reaction device for nucleic acid analysis which is provided with a channel-forming reaction chamber on the substrate (101), the nucleic acid having been immobilized on the microparticles (103) on the substrate (101) is detected. The microparticles (103), which carry the nucleic acid to be detected having been immobilized thereon, are arranged by microstructures (102) aligned on the substrate (101).

7 Claims, 6 Drawing Sheets

(51) Int. Cl.
*G01N 21/64* (2006.01)
*G01N 33/53* (2006.01)
*G01N 33/58* (2006.01)
*G01N 35/00* (2006.01)

(52) U.S. Cl.
CPC ........ *G01N21/6452* (2013.01); *G01N 33/5308* (2013.01); *G01N 33/54373* (2013.01); *G01N 33/582* (2013.01); *B01L 2200/0668* (2013.01); *B01L 2300/0609* (2013.01); *B01L 2300/0877* (2013.01); *B01L 2300/0883* (2013.01); *G01N 35/00* (2013.01); *G01N 2035/00564* (2013.01)

(56) References Cited

U.S. PATENT DOCUMENTS

| | | | |
|---|---|---|---|
| 2003/0044855 A1* | 3/2003 | Anderson et al. | 435/7.9 |
| 2005/0026346 A1* | 2/2005 | Blankenstein et al. | 438/200 |
| 2006/0051807 A1 | 3/2006 | Fuller | |
| 2008/0318244 A1 | 12/2008 | Matsunaga et al. | |
| 2010/0009862 A1 | 1/2010 | Nakahara et al. | |
| 2012/0126142 A1 | 5/2012 | Matsui et al. | |

FOREIGN PATENT DOCUMENTS

| | | |
|---|---|---|
| JP | 2009-512452 A | 3/2009 |
| JP | 2009-180740 A | 8/2009 |
| JP | 2010-110262 A | 5/2010 |
| JP | 2010-243454 A | 10/2010 |
| JP | 2010-286421 A | 12/2010 |

OTHER PUBLICATIONS

J. Shendure et al., "Accurate Multiplex Polony Sequencing of an Evolved Bacterial Genome", Science, vol. 309, Sep. 9, 2005, pp. 1728-1732 (five (5) sheets).

M. Margulies et al., "Genome Sequencing in Microfabricated High-Density Picolitre Reactors", Nature, vol. 437, Sep. 15, 2005, pp. 376-380 (five (5) sheets).

International Search Report with English translation dated Feb. 15, 2011 (four (4) sheets).

R. D. Mitra et al., "Fluorescent in Situ Sequencing on Polymerase Colonies", Analytical Biochemistry, vol. 320, 2003, pp. 55-65 (eleven (11) sheets).

J. Korlach et al., "Selective Aluminum Passivation for Targeted Immobilization of Single DNA Polymerase Molecules in Zero-Mode Waveguide Nanostructures", PNAS, vol. 105, Jan. 29, 2008, pp. 1176-1181 (six (6) sheets).

J. Ju et al., "Four-Color DNA Sequencing by Synthesis using Cleavable Fluorescent Nucleotide Reversible Terminators", PNAS, vol. 103, Dec. 26, 2006, pp. 19635-19640 (six (6) sheets).

T. D. Harris et al., "Single-Molecule DNA Sequencing of a Viral Genome", Science, vol. 320, Apr. 4, 2008, pp. 106-109 (five (5) sheets).

* cited by examiner

NUCLEIC ACID ANALYZER, REACTION DEVICE FOR NUCLEIC ACID ANALYSIS AND SUBSTRATE OF REACTION DEVICE FOR NUCLEIC ACID ANALYSIS

TECHNICAL FIELD

The present invention relates to a nucleic acid analyzer, a reaction device for nucleic acid analysis, and a substrate of a reaction device for nucleic acid analysis.

BACKGROUND ART

New technologies have been developed to determine base sequences of DNA's and RNA's.

In a method utilizing electrophoresis, which is usually used at present, a cDNA fragment sample, which is synthesized in advance from a DNA fragment or an RNA sample for sequence determination by performing a reverse transcription reaction, is prepared, a dideoxy reaction is performed by the well-known Sanger method, and then electrophoresis is performed to measure and analyze a pattern of separated base ladders.

On the other hand, in recent years, a method has been proposed for immobilizing many DNA fragments as samples on a substrate to determine sequence information of many fragments in parallel.

In Non-Patent Literature 1, microparticles are used as carriers for supporting DNA fragments to perform PCR's on the microparticles. After that, the microparticles supporting PCR-amplified DNA fragments are put into a plate provided with many holes, a diameter of which is matched to a size of the microparticles, to read out by a pyrosequence method.

Also, in Non-Patent Literature 2, using the microparticles as supports for supporting DNA fragments, PCR's are performed on the microparticles. After that, the microparticles are scattered and immobilized on a glass substrate, enzyme reactions (ligations) are performed on the glass substrate to let substrates with fluorescent dyes to be incorporated, and sequence information of each fragment is obtained by performing fluorescence detection.

Further, in Non-Patent Literature 3, many DNA probes having the same sequence have been immobilized on a substrate. Also, after scission of a DNA sample, an adapter sequence of a strand complementary to the DNA probe sequence is added to the terminal of each DNA sample fragment. By subjecting these to hybridization on the substrate, the sample DNA fragments are immobilized one molecule by one molecule randomly on the substrate. In this case, after performing DNA elongation on the substrate to let substrates with fluorescent dyes to be incorporated, washing off of unreacted substrates and fluorescence detection are preformed so that sequence information of sample DNA's is acquired.

As described above, a method for immobilizing many DNA fragment samples on a substrate and determining sequence information of many fragments in parallel has been developed and been put into practical use.

CITATION LIST

Non Patent Literature

NON PATENT LITERATURE 1: Nature 2005, Vol. 437, pp. 376-380.
NON PATENT LITERATURE 2: Science 2005, Vol. 309, pp. 1728-1732.
NON PATENT LITERATURE 3: Science 2008, Vol. 320, pp. 106-109.
NON PATENT LITERATURE 4: P.N.A.S. 2006, Vol. 103, pp. 19635-19640.
NON PATENT LITERATURE 5: P.N.A.S. 2008, Vol. 105, pp. 1176-1181.
NON PATENT LITERATURE 6: Anal. Biochem. 2003, Vol. 320, pp 55-65.

SUMMARY OF INVENTION

Technical Problem

However, even when parallel analysis methods as above are used, several days are required to analyze all human genes, and thus an analysis method having further higher throughput has been desired. A plate shown in Non-Patent Literature 1 has a diameter of a hole thereon of 44 μm, and a diameter of the microparticles is 22 μm. There is a problem that density of particles on the plate is low and, thus, the number of the DNA fragments which can be analyzed at once is small. The diameter of the microparticles of Non-Patent Literature 2 is as small as 1 μm and density of the microparticles on the substrate is high. However, because the microparticles are immobilized randomly on the substrate, it is necessary to use a two-dimensional sensor having many numbers of pixels in order to isolate and detect fluorescence from beads which are close together. It has problems of longer data transmission time and decreased throughput of analysis because of increase in the number of data per analysis. In addition, there is also a problem that a detection apparatus becomes expensive because a condensing lens of a large numerical aperture, NA, is necessary. A plurality of reaction solutions are sent to perform ligation reactions and it also causes a problem that the beads are peeled off from the substrate by resistance at the time of sending solutions. Also in Non-Patent Literature 3, arrangement of the DNA sample fragments of measurement objects is random. There is a problem of low throughput and an expensive detection apparatus, similar to in Non-Patent Literature 2.

Solution to Problem

As result of intensive study the inventors of the present invention have completed development of a reaction device for nucleic acid analysis detectable with a two-dimensional sensor having a small number of pixels while yielding high throughput.

This reaction device for nucleic acid analysis is provided with a substrate and a reaction chamber forming a flow channel on the substrate, and is a reaction device for nucleic acid analysis which detects nucleic acids immobilized on carriers on the substrate, wherein microstructures are arranged regularly on the substrate, and wherein each carrier is immobilized by the microstructures.

By the carriers being immobilized by the microstructures arranged regularly, it becomes possible to arrange the immobilized carriers regularly.

Therefore, even when a two-dimensional sensor having a small number of pixels is used, it becomes possible to isolate and detect fluorescence from beads which are close together. Accordingly, since the number of data per analysis decreases, the data transmission time becomes shorter and throughput of analysis is increased. Further, there is no need to use a condensing lens with a large numerical aperture, NA, and the detection device can be made inexpensive.

The present invention is a nucleic acid analyzer comprising a reaction device for nucleic acid analysis with carriers on which nucleic acids to be detected are immobilized arranged regularly on the substrate, an irradiation light source, and a detection unit including a two-dimensional sensor, and it is characterized to include microstructures on the substrate. By giving certain regularity in arrangement or shapes of these microstructures, positions of the carriers can be controlled.

In addition, when the carriers are the microparticles, it is possible to arrange them in high density because their particle diameters are small, and, together, the amount of nucleic acid immobilized on the microparticles can be increased because the shapes of the particles are large in the surface area.

Also, by making the microstructures shorter in the length in a longer direction when viewed from above than the carriers, the microparticles can be arranged in high density.

Further, each one of the above-described microparticles may be present as being surrounded by the microstructures. When a solution containing a reagent is sent onto a substrate on which the microparticles are immobilized, peeling of the carriers (for example, beads) during sending the solution can be prevented directly by contact with the microstructures or indirectly via control of water flow.

Furthermore, by arranging the microstructures in a lattice form, the microparticles can be squarely arranged two-dimensionally in high density conforming with pixel sizes of a two-dimensional sensor.

Besides, because the microparticles are made of a magnetic material, the microparticles can be immobilized on the substrate using magnetic force.

Advantageous Effects of Invention

Using the microstructures arranged along with the pixels of the two-dimensional sensor, the microparticles on which DNA's to be detected are immobilized are immobilized on the substrate. Detection by a two-dimensional sensor having a small number of pixels is enabled. Nucleic acid sequence can be analyzed with high throughput by decreasing the number of data in detection.

DESCRIPTION OF EMBODIMENTS

Explanation is given below on an embodiment of the present invention with reference to drawings.

(Regarding a Substrate and Microparticles Used for a Reaction Device for Nucleic Acid Analysis)

Figure 1:
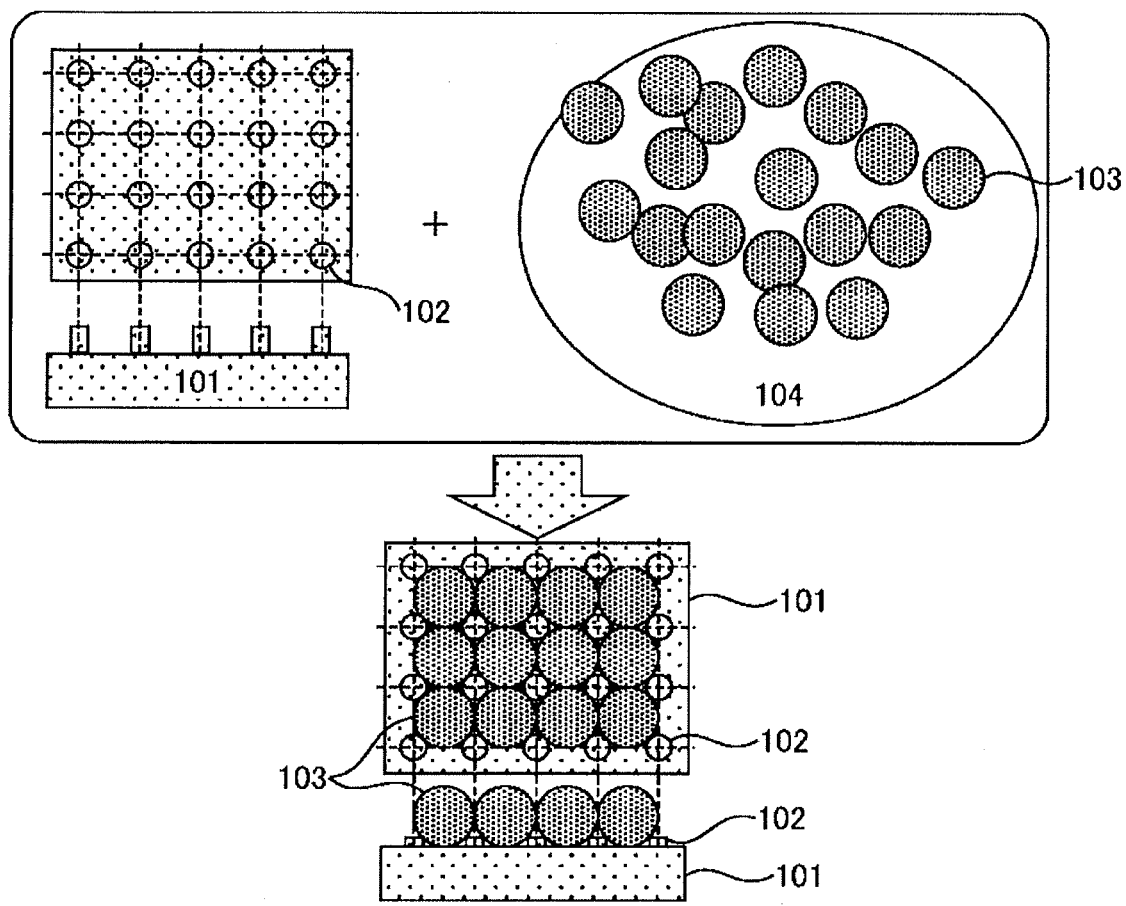
FIG. 1 is a drawing for explaining one example of a configuration of a reaction device for nucleic acid analysis of the present invention.

Explanation is given on a substrate for a reaction device for nucleic acid analysis of the present invention with reference to FIG. 1. Microstructures 102 are arranged on a substrate 101 in a lattice form (the upper left drawing of FIG. 1). Onto the substrate 101 a solution 104 (the upper right drawing of FIG. 1) is sent, which contains the microparticles 103 (which may also be called carriers, or beads) on which nucleic acids to be detected are immobilized. By making the microstructures 102 and the microparticles 103 interact, the microparticles 103 are arranged on the substrate in a lattice form (the lower drawing of FIG. 1).

As the substrate 101, a substrate made of an inorganic substance such as a glass substrate, a sapphire substrate, and a silicon substrate, a substrate made of a metal such as stainless steel, a substrate made of an organic substance such as a polymethylmethacrylate resin, a polycarbonate resin, and a cycloolefin resin, can be used.

As shapes of the microstructures 102, various shapes such as a cylinder, a cone, a triangle pole, a triangular pyramid, and a quadrangular pole can be used. Generally, variations in the shapes or the sizes of these microstructures 102 arise in production even in the same plane. It is preferable that the structures are provided with tapers so that it is possible to contact with the microparticles 103 at any of the positions even when the shapes or the sizes of a plurality of microstructures 102 in contact with one microparticle 103 vary. It should be noted that "tapers" here means such inclinations of the microstructures as becoming thinner from a closer side of the substrate to a further side.

A material of the microstructures 102 is not especially limited, as long as it can be finely processed to equal to or smaller than the diameter of the microparticles 103. As a combination of such a material and a processing method, a combined processing of photolithography and dry etching in silicon, nanoimprint lithography in a polymethylmethacrylate resin or a cycloolefin resin; or the like can be listed.

The microstructures 102 and the microparticles 103 are immobilized via various bondings. As such bonding schemes, hydrophobic bonding, electrostatic interaction, covalent bonding, and the like can be used. If it is electrostatic interaction, by introducing amino groups on the surfaces of the microstructures, the microparticles 103 adsorbing DNA's efficiently can be immobilized. Also, if it is covalent bonding, by introducing in advance amino groups or sulfide groups at the terminals of immobilized DNA's of the microparticles 103, for example, and making reaction with functional groups on the surfaces of the substrate 101 and the microstructures 102 via linker molecules, firm bonding can be attained. By using such chemical bonding, peeling or dropping of the microparticles 103 in sending a solution for washing or the like can be prevented.

In introduction of functional groups onto the substrate surface, it is necessary to select a suitable method in consideration of a material thereof; for example, when the material is an organic resin, introduction of hydroxyl groups or carboxyl groups by oxidation treatment, graft polymerization of monomer molecules having desired functional groups, or the like can be listed.

As a linker molecule, although it should be selected in consideration of combination of functional groups of the substrate 101 and the DNA terminals, for example, a molecule having a sulfohydryl group, an amino group, a carboxyl group, a phosphate group, an aldehyde group, or the like can be used. Also, functional groups on the surfaces of the microparticles in addition to functional groups at the DNA terminals can also be utilized. For example, in many cases the surfaces of the microparticles have carboxyl groups to enhance dispersibility, and these carboxyl groups and carboxyl groups generated on the substrate surfaces by oxidation treatment or graft polymerization of an organic substrate can be immobilized using molecules having a plurality of amino groups, represented by polyamine, and a reagent such as carbodiimide. In addition, a metal ion can be used as a linker. For example, a tetravalent Zr ion has been known to exhibit interactions with a carboxyl group and a single-stranded DNA; the tetravalent Zr ion is immobilized using a carboxyl group generated on the surface by, for example, oxidation treatment or graft polymerization of the surface of an organic substrate so that immobilization is possible using interaction of the Zr ion thereof and a single-stranded DNA.

Incidentally, use of such a linker is not essential, and it is possible to bond the substrate 101 and the microparticles 103, for example, via a carboxyl group generated by oxidation of an organic substrate, and an amino group introduced at the DNA terminal on the surfaces of the microparticles. As the microparticles 103, those having a diameter of 5 nm to 100 nm are available on the market, and they can be utilized. A material composing the microparticles includes polystyrene, a magnetic material represented by iron oxide, semiconductor microparticles, or the like, and the magnetic material, where magnetic force can be utilized for alignment, is particularly preferable.

As a method for forming the microstructures 102 on the substrate 101, when a smooth material is an inorganic material, thin-film processing, which is already put into practice for a semiconductor, may be utilized. For example, it can be manufactured by vapor deposition or sputtering deposition through a mask, or dry or wet etching after formation of a thin film by vapor deposition or sputtering deposition. On the other hand, when a material of the substrate 101 is an organic material such as PMMA, a molding scheme like nanoimprint may also be used.

(Regarding a Reaction Device for Nucleic Acid Analysis)

Figure 2:
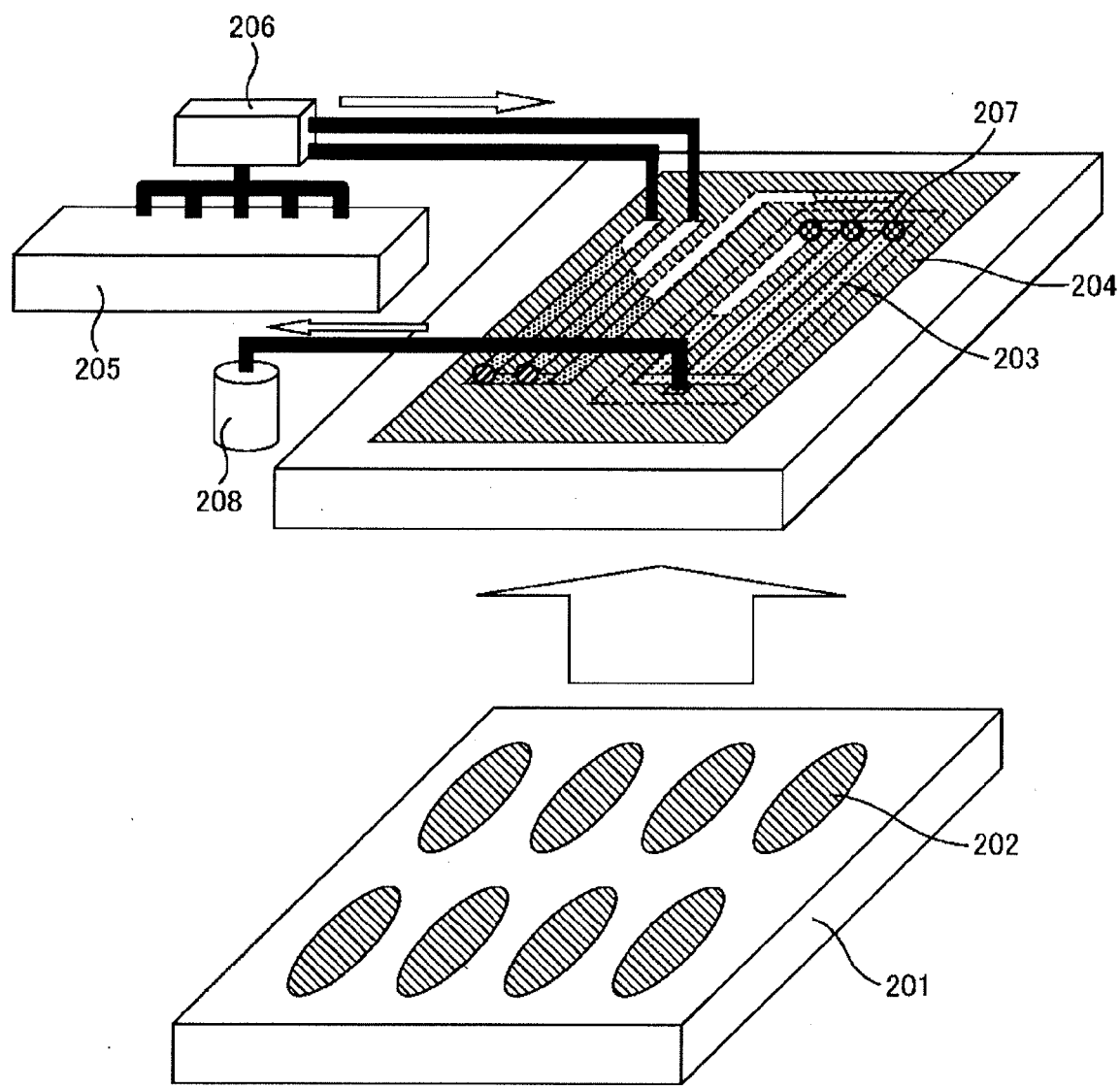
FIG. 2 is a drawing for explaining one example of a configuration of a reaction device for nucleic acid analysis of the present invention.

Explanation is given on an example of a preferable configuration of a reaction device for nucleic acid analysis of the present invention with reference to FIG. 2. On a substrate 201, a plurality of regions 202 are mounted, where the microparticles (not shown) are arranged in a lattice form. Spacings of the regions 202 can be set properly according to a nucleic acid sample to be analyzed and specifications of a fluorescence detection device. Installation of a plurality of reaction regions on the substrate 201 can be attained by covering a reaction chamber 204 provided with flow channels 203 in advance on the optically transparent substrate 201. The reaction chamber 204 is made of a base substance of a resin such as PDMS (polydimethylsiloxane) on which grooves of the channels 203 are excavated in advance to form channels, and is used as being pasted together on the substrate 201. The reaction device for nucleic acid analysis produced by pasting can be used together with a temperature control unit 205 for storing and managing temperature of a nucleic acid sample, a reaction enzyme, a buffer, a nucleotide matrix, or the like, a dispensing unit 206 for sending a reaction solution out, valves 207 for controlling liquid flows, and a waste liquid tank 208. Temperature is controlled by arranging a temperature controller as needed. After completion of a reaction, a cleaning solution is supplied through the channels 203 and stored in a waste liquid tank 208.

(A Manufacturing Method of a Substrate for the Reaction Device for Nucleic Acid Analysis)

Figure 3:
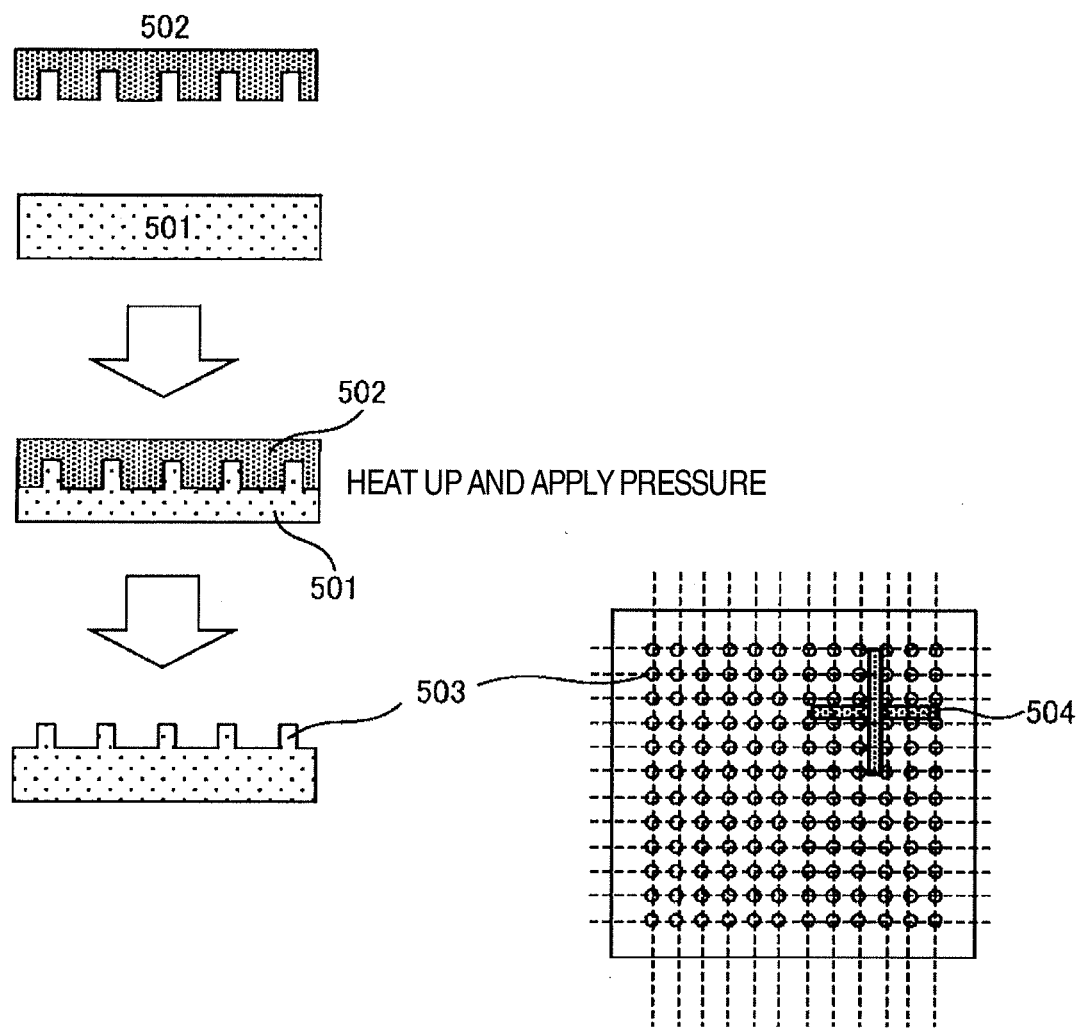
FIG. 3 is a drawing for explaining one example of a manufacturing method of a reaction device for nucleic acid analysis of the present invention.

Explanation is given on a manufacturing method of a substrate for the reaction device for nucleic acid analysis with reference to FIG. 3. On a substrate 501 made of a thermoplastic resin such as a cycloolefin resin (Zeonor 1060R manufactured by Zeon Corp.) microstructures 503 are produced using a stamper 502. The substrate 501 having the microstructures 503 is obtained by a nanoimprint lithography method, in which the stamper 502 is pressed against the substrate 501 heated up to glass transition temperature or higher. In this case, the stamper 502 has a depression or a protrusion of a cross hair or a marker like a cross hair except for missing its center portion, and a marker 504 is also formed simultaneously on the substrate 501 having the microstructures 503. By producing this marker 504, arrangement positions and angles of the microstructures 503 can be estimated to estimate final positions of the microparticles, even from a low magnification image in which the microstructures 503 can not be directly observed.

Incidentally, the explanation was given on an example where the microstructures are arranged in a lattice form in FIG. 3. An arrangement method is not limited to this, however, and it can be varied freely to match with arrangement of CCD elements. For example, when a rectangular pixels CCD is used, in which arrangement intervals of light receiving elements composing the CCD are different in a longitudinal direction and a lateral direction, the microstructures may be arranged with different intervals in a longitudinal direction and a lateral direction in agreement with arrangement intervals of the light receiving elements. Also, when it is a CCD with its light receiving elements being in a honeycomb structure, for example, it may be arranged in a square lattice form inclined by 45 degrees from the arrangement angle of the CCD.

Further, not being limited to line up the microstructures in a constant interval, such an arrangement may also be adopted that, for example, an interval between the first line and the second line is short, an interval to the next third line is long, and an interval to the fourth line is short again.

(Regarding Other Variations of the Substrate for the Reaction Device for Nucleic Acid Analysis)

Figure 5:
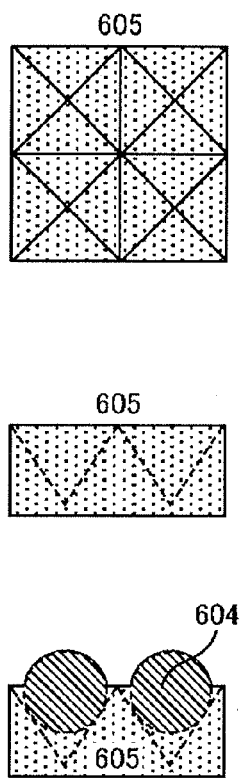
FIG. 5 is a drawing for explaining another variation of microstructures in a device for nucleic acid analysis of the present invention.
Figure 6:
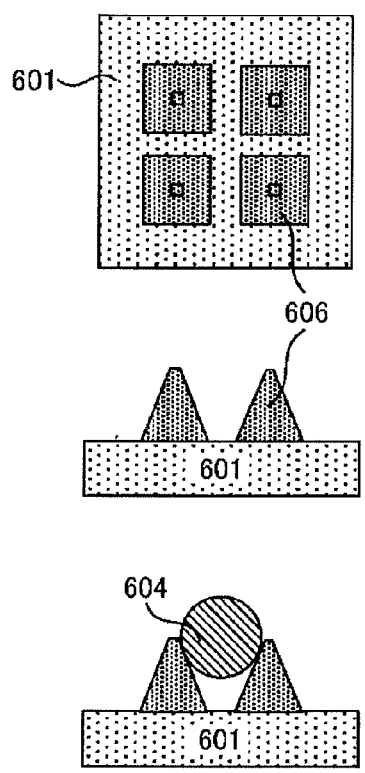
FIG. 6 is a drawing for explaining another variation of microstructures in a device for nucleic acid analysis of the present invention.

The microstructures formed on a substrate 601 used for the reaction device for nucleic acid analysis are not limited to the ones described above, and may be those explained below. Namely, other microstructures suitable for a substrate 601 used for the reaction device for nucleic acid analysis are explained with reference to FIGS. 4 to 6.

The microstructures may be those composed of the first microstructures 602, and the second microstructure 603, the center point of which is inside of a square formed by the center points thereof. This second microstructure 603 is characterized to be lower in the height from the plane of the substrate 601 compared with the first microstructures 602. Such the second microstructure 603 can be produced, for example, by using OEBR, ZEP2000, or the like, which is an analog-type resist, and by reducing the exposure dose in electron beam lithography of 603 compared with 602. Alternatively, it may be produced by creating a stamper using a substrate having the first microstructures 602 as a master and using a nanoimprint lithography method as in FIG. 3. By immobilizing microparticles 604 while floating from the substrate using the substrate having two or more kinds of the microstructures 602, 603 with different heights like the above, it becomes possible to mitigate ghost imaging of intrinsic fluorescence from the substrate 601 during observation of the microparticles. Further, by providing space underneath the microparticles 604, a matrix can be supplied uniformly to the surfaces of the microparticles 604, which are fields of reaction, and enhancement of enzyme reaction efficiency becomes possible. By this, in the case of, for example, sequencing reactions shown in a nucleic acid analysis method described below, phase shifts can be prevented and reading of longer base lengths becomes possible. Also, by making the microparticles 604 float from the substrate surface, shortening of cleaning time can be attained due to enhancement of cleaning efficiency of the surfaces of the microparticles so that overall throughput is improved. Further, a phenomenon could occur that part of a reagent in a previous reaction cycle remains and reacts in a subsequent cycle in a reaction system such as shown in a nucleic acid analysis method described below, but by enhancing washability it becomes possible to reduce the amount of residue of the reagent by each cycle, yielding enhancement of reliability of data.

Figure 4:
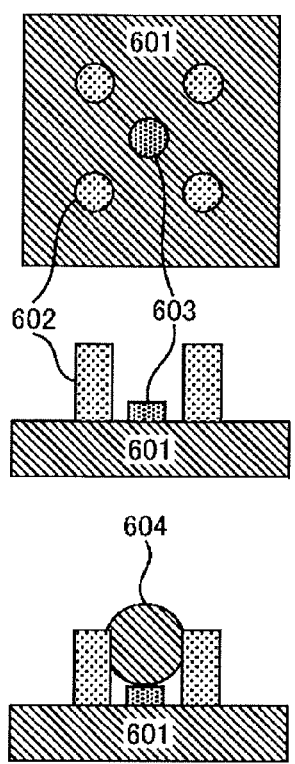
FIG. 4 is a drawing for explaining another variation of microstructures in a device for nucleic acid analysis of the present invention.

Incidentally, in FIG. 4, the top drawing is a plan view showing the substrate 601 before the microparticle 604 is immobilized, the second drawing from the top is a cross-sectional view of the substrate 601 before the microparticle 604 is immobilized, and the bottom drawing is a cross-sectional view of the substrate 601 after the microparticle is arranged. With regard to this point, it is similar also in FIG. 5 and FIG. 6.

As structures for providing space underneath the microparticles 604 like the above, there are inverted pyramid structures 605 (FIG. 5) or truncated pyramid structures 606 (FIG. 6), or the like. These structures can be obtained by anisotropic etching of Si or the like. It should be noted that the inverted pyramid structures are produced by forming trenches on a substrate.

(Regarding a Nucleic Acid Analyzer)

Figure 7:
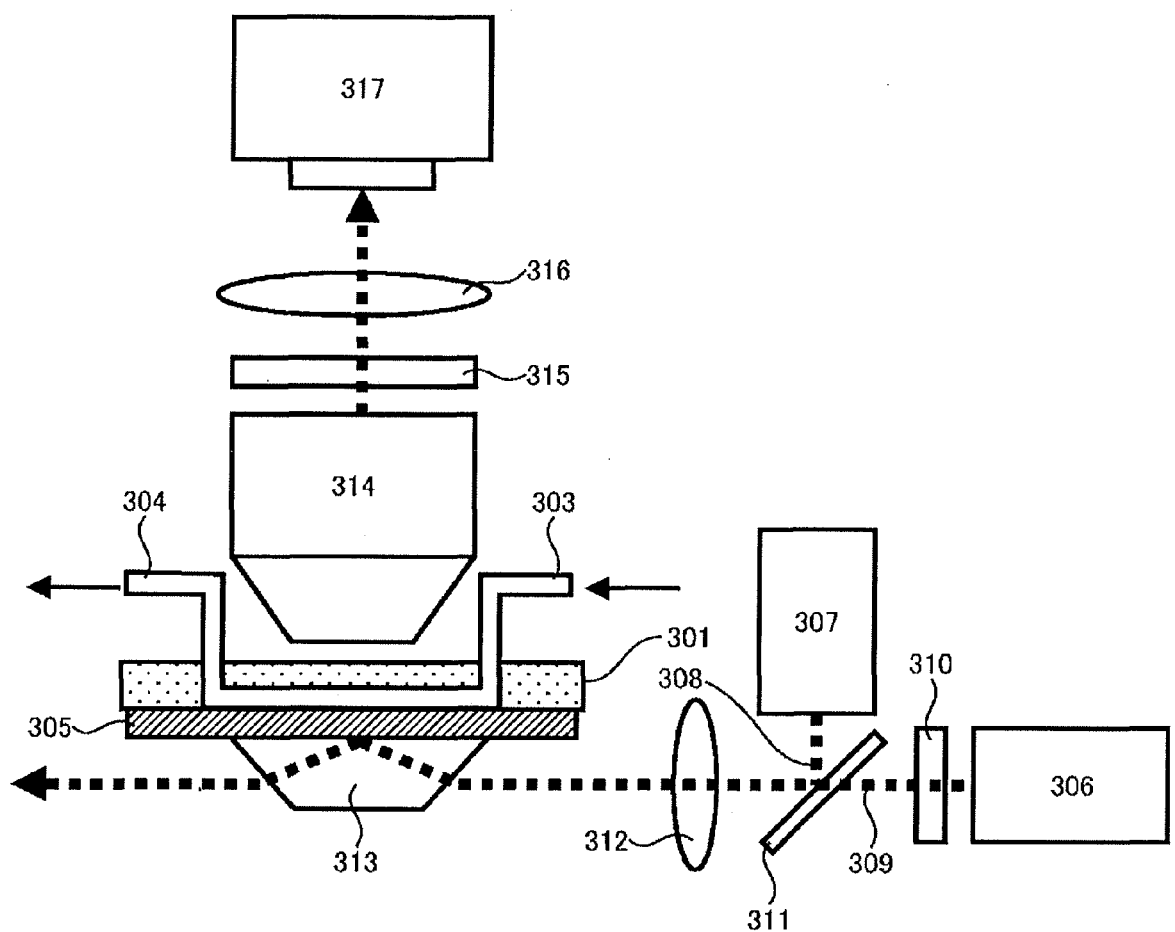
FIG. 7 is a drawing for explaining one example of a configuration of a reaction apparatus for nucleic acid analysis of the present invention.

Explanation is given on a nucleic acid analyzer of the present invention with reference to FIG. 7. A nucleic acid analyzer is provided with a means which supplies one or more kinds of biomolecules consisting of nucleotides, nucleotides having fluorescent dyes, nucleic acid synthetases, primers, and a nucleic acid sample, to a reaction device for nucleic acid analysis; a means which irradiates the reaction device for nucleic acid analysis with light; and a fluorescence detecting means which measures fluorescence of a fluorescent dye incorporated in a nucleic acid strand by a nucleic acid elongation reaction which occurs by co-presence of the nucleotides, the nucleic acid synthetases, and the nucleic acid sample on the reaction device for nucleic acid analysis.

More specifically, a substrate 305 is installed to a reaction chamber composed of a cover plate 301 equipped with a channel in advance and an inlet 303 and an outlet 304 which are openings for exchange of solutions. Incidentally, as a material of the cover plate 301, PDMS (polydimethylsiloxane) is used. After adjusting laser light 308 and 309 oscillating from an YAG laser light source (a wavelength of 532 nm and an output of 20 mW) 306 and an YAG laser light source (a wavelength of 355 nm and an output of 20 mW) 307 by a dichroic mirror 311 (which reflects light with a wavelength of 410 nm or shorter) so that the two of laser light are coaxial, they are concentrated by a lens 312, and then are incident onto the substrate 305 via a prism 313 in a critical angle or greater. Fluorescence emitted from the cover plate 301 is converted to a collimated luminous flux by an objective lens 314, background light and excitation light are blocked by an optical filter 315, and an image is formed on a two-dimensional CCD camera 317 by an imaging lens 316.

Figure 8:
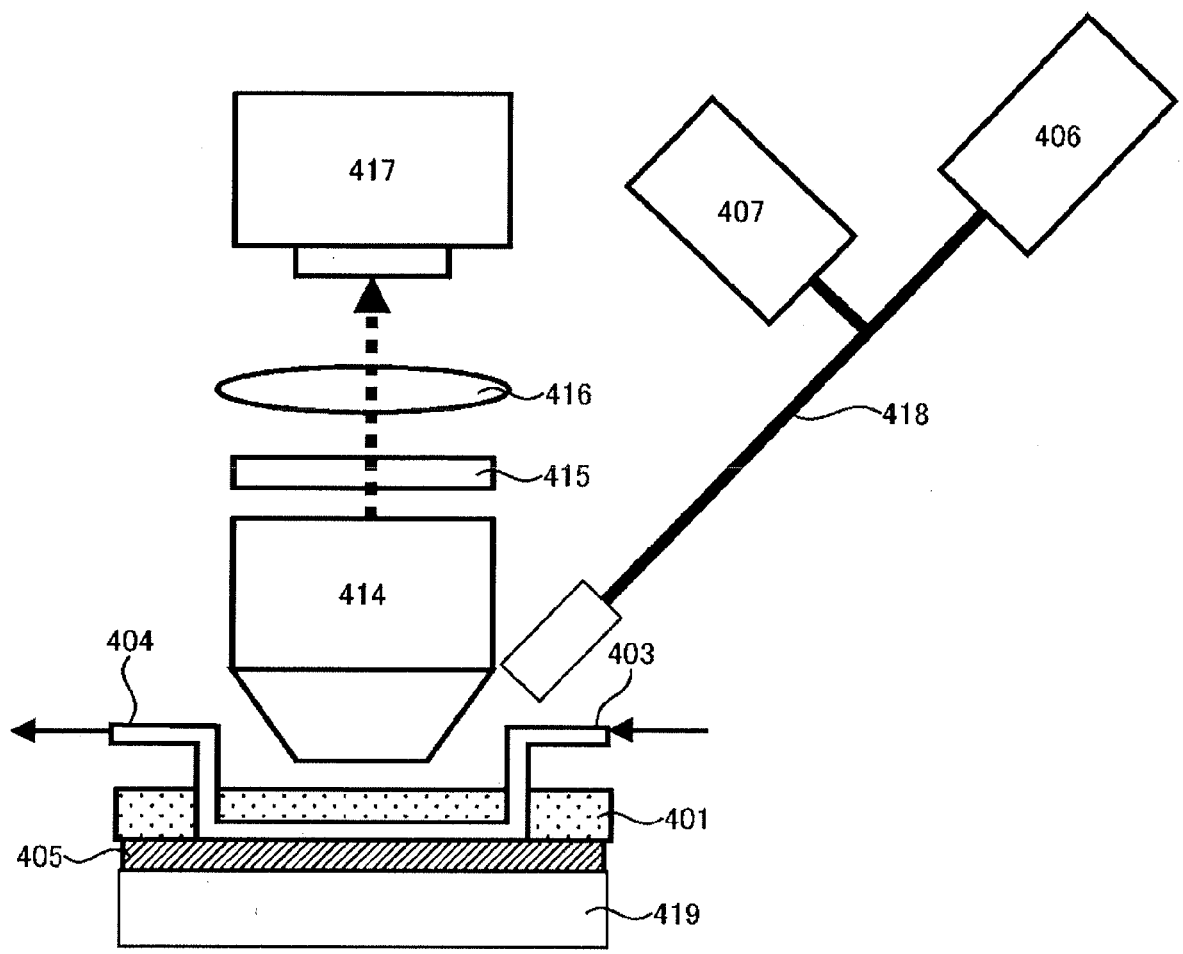
FIG. 8 is a drawing for explaining one example of a configuration of a reaction apparatus for nucleic acid analysis of the present invention.

Explanation is given on a variation example of the nucleic acid analyzer shown in FIG. 7 with reference to FIG. 8. Differences from the nucleic acid analyzer shown in FIG. 7 are installment of a temperature control element 419 under the reaction device and irradiation of laser light generated from light sources 406 and 407 via an optical fiber 418. Because the reaction device is in direct contact with the temperature control element 419, temperature difference between the temperature control element 419 and temperature of the solution on the reaction device can be made small, and efficiency of the sequencing reactions can be enhanced. 406 and 407 are laser light sources to radiate toward the reaction device from squares (opening parts) at their tips via the optical fiber 418.

(Regarding a Nucleic Acid Analysis Method Using the Reaction Device for Nucleic Acid Analysis and the Nucleic Acid Analyzer)

In accordance with a method disclosed in Non-Patent Literature 2, after fragmentation and amplification of a DNA of a measurement object, beads on which the DNA fragments of measurement objects are immobilized are produced using the emulsion PCR method. Subsequently, in accordance with a method disclosed in Non-Patent Literature 6, the beads are immobilized on the reaction device for nucleic acid analysis of the present invention using acrylic gel. Next, the reaction device for nucleic acid analysis on which the beads are immobilized is installed to the nucleic acid analyzer shown in FIG. 8. Finally, in accordance with a method disclosed in the Non-Patent Literature 2, the following actions are performed to determine base sequences:

(1) hybridization of anchor primers,
(2) ligation of fluorescent primers,
(3) detection of fluorescence,
(4) removal of the anchor primers and the fluorescent primers, and
(5) repeat of (1) through (4).

Also, the present invention can use the successive reaction scheme other than the method by the above ligation. As nucleotides with fluorescent dyes, the one with a 3'-O-allyl group introduced as a protecting group at the 3' OH position of ribose and with fluorescent dyes via allyl groups bound at the 5-position of pyrimidines or at the 7-position of purines can be used as disclosed in Non-Patent Literature 4. Since the allyl groups are cleaved by light irradiation or contact with palladium, quenching of the dyes and control of the elongation reactions can be attained simultaneously. Even in the successive reaction, removal of unreacted nucleotides by cleaning is not necessary.

Further, in the present embodiment, since a cleaning step as shown in Non-Patent Literature 5 is not required, elongation reactions can also be measured in real time. As described above, by constructing the nucleic acid analyzer using the reaction device for nucleic acid analysis of the present embodiment, shortening of analysis time and simplification of the reaction device and the analyzer can be plotted without introducing a cleaning step, the elongation reactions of bases can also be measured not only in the successive reaction scheme but also in real time, and significant improvement of the throughput with respect to conventional technology can be designed.

REFERENCE SIGNS LIST 101, 201, 305, 501, 601 substrate
102, 503 microstructures
103, 604 microparticles
104 solution
202 regions where the microparticles are arranged in a lattice form
203 channel 204 reaction chamber
205 temperature control unit
206 dispensing unit
207 valve
208 waste liquid tank
301 cover plate
303 inlet
304 outlet
306, 307 YAG laser light source
308, 309 laser light
310 dichroic mirror
312 lens
313 prism
314 objective lens
315 optical filter
316 imaging lens
317 two-dimensional CCD camera
418 optical fiber
419 temperature control element
502 stamper
504 marker
602 first microstructures
603 second microstructures
605 inverted pyramid structures (microstructures)
606 square pole structures (microstructures)

The invention claimed is:

1. A reaction device for nucleic acid analysis which detects nucleic acids, comprising:
   a substrate;
   a carrier disposed on the substrate, wherein the nucleic acids are immobilized on the carrier; and
   a reaction chamber, having a flow channel, disposed on the substrate, the reaction chamber having a shape of a channel;
   wherein microstructures in the form of protrusions are arranged regularly on the substrate within the reaction chamber, the microstructures comprising a first microstructure; and four second microstructures which are positioned in a rectangular pattern and are taller in height of protrusions from the substrate than the first microstructure, the first microstructure being provided at a center of the rectangular pattern of the four second microstructures,
   wherein the carrier is immobilized by the microstructures so that a bottom part of the carrier is spaced apart from the substrate; and
   wherein the carrier can be immobilized in contact with the first microstructure and the four second microstructures.

2. The reaction device for nucleic acid analysis according to claim 1, wherein the microstructures are arranged in a lattice form.

3. The reaction device for nucleic acid analysis according to claim 1, wherein a functional group for capturing the carrier is introduced to the substrate.

4. The reaction device for nucleic acid analysis according to claim 1, wherein the carrier comprises a magnetic material.

5. The reaction device for nucleic acid analysis according to claim 1, wherein the carrier is microparticle.

6. A substrate for a reaction device for nucleic acid analysis used to detect nucleic acids, comprising:
   a carrier disposed on the substrate, wherein the nucleic acids are immobilized on the carrier; and
   microstructures in the form of protrusions regularly arranged on the substrate, the microstructures comprising a first microstructure; and four second microstructures which are positioned in a rectangular pattern and are taller height of protrusions from the substrate than the first microstructure, the first microstructure being provided at a center of the rectangular pattern of the four second microstructures;
   wherein the carrier can be immobilized in contact with the first microstructure and the four second microstructures.

7. The substrate for a reaction device for nucleic acid analysis according to claim 6, wherein the microstructures are arranged in a lattice form.

* * * * *